US00PP10980P

United States Patent [19]

Saville

[11] Patent Number: Plant 10,980

[45] Date of Patent: Jun. 29, 1999

[54] MINIATURE ROSE PLANT NAMED 'SAVABINO'

[75] Inventor: F. Harmon Saville, deceased, late of Newburyport, Mass., by Charles K. Brown, executor

[73] Assignee: Nor'East Miniature Roses, Inc., Rowley, Mass.

[21] Appl. No.: 08/990,338

[22] Filed: Dec. 15, 1997

[51] Int. Cl.[6] ..... A01H 5/00

[52] U.S. Cl. ..... Plt./120

[58] Field of Search ..... Plt./119, 120, 116, Plt./122

[56] References Cited

U.S. PATENT DOCUMENTS

P.P. 6,617 2/1989 Moore ..... Plt./118

*Primary Examiner*—Howard J. Locker

[57] ABSTRACT

SAVabino is a miniature rose which can be grown quite satisfactorily in a greenhouse, indoors under lights or as a hardy garden perennial. It blooms continually throughout the growning season with buds and flowers of red-orange. Blooms are most often borne in clusters on a small, compact plant that is no more than 14 inches tall.

1 Drawing Sheet

BACKGROUND OF THE INVENTION

1. This present invention relates to a new and distinct variety of hardy, bush type plant of the miniature rose class, whose flower petals, open bloom and bud are similar in form to but larger in size than those of RUImired (U.S. Plant Pat. No. 5,770, sold and marketed as Red Minimo), and whose coloring of its outer petals is similar to that of MEIgabi (U.S. Plant Pat. No. 2,646, also listed as MEIgali and sold and marketed as Starina). This invention can be grown quite satisfactorily indoors under lights, in a greenhouse, and as a garden perennial, with protection recommended through the winter in sever climates.

2. This present invention is a new and distinct variety of miniature rose plant (*Rosa chinensis* 'minima'), which was created by crossing the following two rose plants: The seed parent is MORsegold, (U.S. Plant Pat. No. 6,617), a prolific miniature rose, with medium yellow flowers, created by Ralph Moore in 1986, sold and marketed as Sequoia Gold. The pollen parent is Savaspark (U.S. Plant Pat. No. 9,799) a scarlet red miniature created by F. Harmon Saville and sold and marketed as Sparks. The varietal denomination of this new rose is SAVabino.

This new variety is distinguished by:

A. A vigorous, well branched, compact habit.
B. Flowers borne mostly in small clusters.
C. Orange-red blooms on a miniature plant.

Asexual production by cuttings of this new variety as performed in Essex County, Mass. and in San Bernardino County, Calif. shows that all distinguishing characteristics of this rose continually come true to form.

SUMMARY OF THE INVENTION

This new variety has small red-orange flowers, borne mostly in clusters. The plant itself is small, well branched and compact growing to only 14 inches tall at maturity. It can be grown quite satisfactorily inside under lights, in a greenhouse or as a hardy garden perennial requiring winter protection in severe climates.

BRIEF DESCRIPTION OF THE DRAWING

The accompanying color photograph shown specimens of the flowers of this new variety in different stages of development as seen and grown inside under plastic in August in Essex County, Mass.

BOTANICAL DESCRIPTION OF THE PLANT

Following is a detailed description in outline form pertaining specifically to this new and distinct variety of miniature rose plant. All major color plate identifications made are referring to The Royal Horticulture Society Colour Chart except where common terms of color definition are employed.

Type: Miniature rose; hardy; outdoors; decorative; potted plant; greenhouse; indoors under lights.
Seed parent: MORsegold, U.S. Plant Pat. No. 6,617.
Pollen parent: SAVaspark, U.S. Plant Pat. No. 9,799.
Flowers: Usually borne in small clusters.
Quantity of bloom: Profuse.
Bud:
- *Size and form.*—Small, obtuse with sepals lending the illusion of an acute tip.
- *Sepals.*—Lanceolate, 2 inner sepals finely bearded, 3 outer sepals have smooth edges with 0 to 2 "flags" on each edge and having the appearance of being barbed at the ends where they extend beyond the tip of the bud, rolling back just ahead of the petals, folding back almost to the stem as the bloom matures, and remaining permanently attached; near 144A in color.
- *Color when sepals first divide.*—Near 43A.
- *When petals begin to unfurl.*—Between near 40B and 43B and usually with 15D from base and blending upward.
- *Peduncle.*—Varying from ⅞ to 1⅛ to 1¼ inches; straight; erect; near 144B in color.

Bloom:
- *Size when fully expanded.*—1⅛ to 1¼ inches.
- *Borne.*—Mostly in clusters of 3 or 4 and sometimes up to 7, but also occasionally singly.
- *Form.*—Opening flat, petals becoming and remaining loosely rolled outward.

*Petalage under normal conditions.*—27 to 39 with 2 to 5 petaloids in the center; petaloids often have a light yellow streak in them.

*Fragrance.*—None.

Petals:

*Texture.*—Medium to thin, inside velvety, outside satiny.

*Form.*—Spatulate, outer petals being much wider than inner petals.

*Arrangement.*—Petals overlapping in an irregular pattern.

Color (From plants grown inside under plastic in Essex County, Mass., in Aug. 1997):

*During first two days.*—(Outer petals) inside surface—between near 44B and 34A, reverse—between 40C and near 33B and between near 15B and 15C blending uip from base. (inner petals) inside surface—between near 40B and near 43B, reverse—between 33A and near 44C at upper outer edge, near 16A at lower outer edges, and 15D from the center of the base and blending up and out into the other colors.

*When half blown.*—(Outer petals) inside surface—near 40C and near 5A at base, reverse—near 44D blending with near 22B from base. (inner petals) inside surface—between near 34A and near 44C and near 9B at base with occasional streaks of 18B, reverse—between 40C and near 33B with near 15C blending up from base.

*Base of petals at attachment.*—Near 5A.

*Color change as bloom ages.*—From near 43B to near 40B, and then to a color between 44B and 34A with a color between 40B and 43B towards center, then to near 40C with a color between 34A and 44C towards center and an occasional streak of near 18B, to near 43C on outer petals and inner petals of near 41D and becoming near 8B towards center of bloom, then finally becoming near 50B on outer edges with a mix of near 39C and near 49C and near 50C on outer edges of inner petals but with near 18B at the center and becoming near 18C and lighter as it blends outward and into the mix of coloring from the outer edges.

*General tonality.*—Red-orange; after three or more days—the red-orange color is lightened as the yellow at the base of each petal expands and blends outward into the petal.

Lasting quality:

*On plant.*—5 or more days, and petals remaining attached and dropping with peduncle after both have dried.

*As a cut flower.*—3 to 5 days.

Reproductive organs:

*Stamens.*—Few; arranged in small clusters along upper, outer edge of receptacle.

*Filaments.*—Very short, varying to less than 1/16 of an inch; light green-yellow color.

*Anthers.*—Near 163C in color.

*Pollen.*—Very small amount; near 22A in color.

*Pistils.*—Few.

*Styles.*—Uneven in length, to 1/16 of an inch; light red color.

*Stigmas.*—Color near 38D.

*Hips.*—None observed.

The plant:

*Habit.*—Spreading, well branched, very compact.

*Growth.*—Vigorous, uniformly branched, 14 inches tall and spreading to 20 inches.

*Length of flowering stem.*—Up to 3" when borne singly.

*Foliage.*—Small, abundant, compound of three to five leaflets. Color: new foliage, upper surface—near 146A and the serration at the edges may be flushed with near 176A; underside—near 146B and may be flushed with near 176B except along the leaf stem. Old foliage, upper surface—near 147A; underside—near 191A.

*Leaflet.*—Shape—oval pointed; texture, upper surface—(semi glossy new growth) matte older growth, under side—matte; edge—fine, uneven serration.

*Rachis.*—Color, upper surface—near 147B, underside—between 147C and 146C.

*Stipules.*—Heavily and coarsely bearded, up to 5/8 of an inch in length.

*New wood.*—Smooth with a color near 144A.

*Old wood.*—Near 144B and with slightly raised areas of near 199A.

*Resistance to diseases.*—Average.

*Thorns.*—1/8" in length, very thin, pointed, straight and angled down; color when young: near 181B at the base and becoming 154D at the tip. On main stalk: few. On laterals from main stalk: only a few prickles.

*Prickles.*—Only one or two on the main stem of each leaf and on laterals.

The miniature rose plant and its flowers described herein may vary in detail due to climate, soil and cultural conditions under which the variety may be grown; the present description being of the new variety as grown inside under plastic in Essex County, Mass. in August.

It is claimed:

1. A new and distinct variety of miniature rose plant of hardy, well branched and spreading yet compact, miniature habit, substantially as illustrated and described, characterized by small red-orange flowers fading to a lighter orange, borne most often in small clusters, bicolor thorns and heavily foliated sepals, and easy to propagate from cuttings.

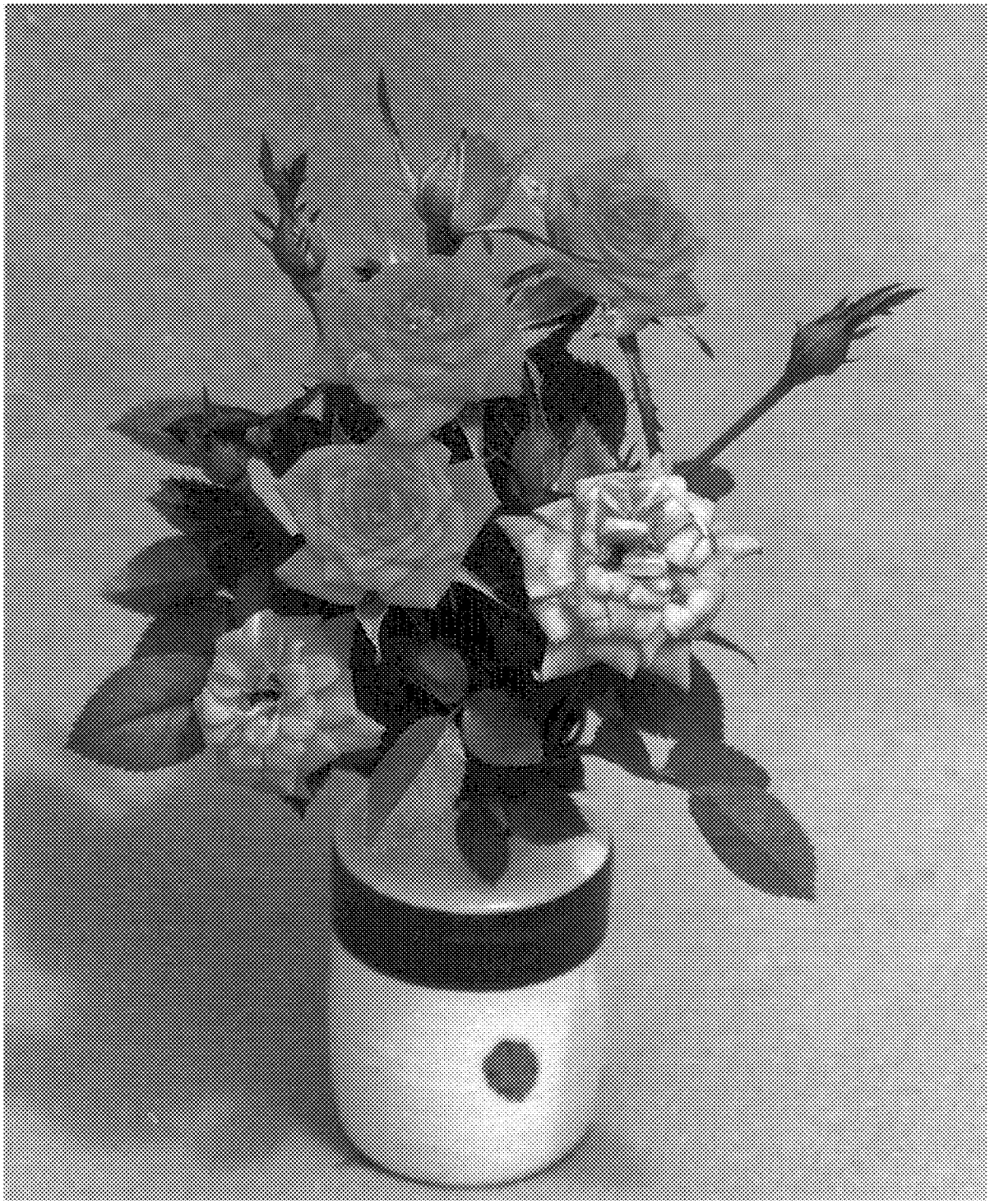

* * * * *